United States Patent
Ohara

(10) Patent No.: US 7,652,262 B2
(45) Date of Patent: Jan. 26, 2010

(54) RADIOGRAPHIC IMAGE DETECTING APPARATUS AND RADIOGRAPHIC IMAGING SYSTEM

(75) Inventor: Hiromu Ohara, Hachioji (JP)

(73) Assignee: Konica Minolta Medical & Graphic, Inc., Tokyo (JP)

( * ) Notice: Subject to any disclaimer, the term of this patent is extended or adjusted under 35 U.S.C. 154(b) by 411 days.

(21) Appl. No.: 11/813,466

(22) PCT Filed: Jan. 30, 2006

(86) PCT No.: PCT/JP2006/301418

§ 371 (c)(1),
(2), (4) Date: Jul. 6, 2007

(87) PCT Pub. No.: WO2006/080485

PCT Pub. Date: Aug. 3, 2006

(65) Prior Publication Data

US 2009/0278051 A1    Nov. 12, 2009

(30) Foreign Application Priority Data

Jan. 31, 2005   (JP) ............................. 2005-023778

(51) Int. Cl.
  *H01L 27/146* (2006.01)
(52) U.S. Cl. .................................. 250/390.09
(58) Field of Classification Search ..............
              250/370.01–370.15, 390.09; 378/98.8
  See application file for complete search history.

(56) References Cited

U.S. PATENT DOCUMENTS

2006/0054833 A1*  3/2006  Tsuchino et al. ....... 250/370.11

FOREIGN PATENT DOCUMENTS

| JP | 2002224095 | 8/2002 |
| JP | 2004147084 | 5/2004 |
| JP | 2004188095 | 7/2004 |
| JP | 2005013310 | 1/2005 |

* cited by examiner

*Primary Examiner*—David P Porta
*Assistant Examiner*—Kiho Kim
(74) *Attorney, Agent, or Firm*—Lucas & Mercanti, LLP

(57) ABSTRACT

A radiographic imaging system 1 of the present invention includes: a radiographic image detecting apparatus 6 to obtain radiographic image data; a console 7 to operate the radiographic image detecting apparatus, the console including a display unit 17 for displaying the obtained radiographic image data; and an image storage device 2 which is communicable with the radiographic image detecting apparatus and the console through a network 8, wherein the radiographic image detecting apparatus transmits the obtained radiographic image data to the image storage device, and generates confirmation radiographic image data has a small amount of data based on the information and transmits the information to the console, the image storage device stores the transmitted radiographic image data, and the console displays the transmitted confirmation radiographic image data on the display unit.

4 Claims, 4 Drawing Sheets

RADIOGRAPHIC IMAGE DETECTING APPARATUS AND RADIOGRAPHIC IMAGING SYSTEM

TECHNICAL FIELD

The present invention relates to a radiographic image detecting apparatus and a radiographic imaging system, for radiographing a radiographic image represented by an X-ray image.

BACKGROUND ART

Heretofore, in the medial diagnosis, a radiographic image which is obtained by irradiating a subject with a radiation such as an X-ray and by detecting an intensity distribution of the radiation transmitted through the subject, has been widely used. Moreover, in recent years, there has been proposed a radiographic imaging system using an FPD (Flat Panel Detector) as a radiographic image detecting apparatus that converts the radiation into electrical signals and detects the electrical signals as radiographic image data during the radiographing.

In the radiographic imaging system, there is known the one composed so as to be used by being connected to a predetermined console, such as a PC (Personal Computer), for operating the FPD placed in a radiographing room through a predetermined communication line in order to enhance a degree of freedom in a system configuration (for example, refer to Patent Document 1).

Moreover, a cassette-shaped FPD which contains the FPD in a cassette for the purpose of enhancing portability and usability of the FPD, has also been developed (for example, refer to Patent Document 2).

Furthermore, the system in which the cassette-shaped FPD and the console are constructed as a system so as to be capable of wirelessly communicating various information such as the radiographic image therebetween, has also been proposed (for example, refer to Patent Document 3).

Here, in general, it is necessary to confirm whether or not the radiographing has been appropriately performed after the radiographing. Accordingly, in the conventional radiographic imaging system, the radiographic image data detected by the FPD is transmitted to the console connected through the communication line, and based on the radiographic image data received from the FPD, image data (confirmation radiographic image data) of a reduced image such as a thumbnail image is generated by the console and displayed on a display unit. Therefore, a radiographing state is confirmed (for example, refer to Patent Document 4).

Patent Document 1: JP-Tokukai-2003-199736A
Patent Document 2: JP-Tokukai-Hei-6-342099A
Patent Document 3: JP-Tokukai-2003-210444A
Patent Document 4: JP-Tokukai-2002-224095A

DISCLOSURE OF THE INVENTION

Problem to be Solved by the Invention

Incidentally, in the conventional radiographic imaging system, there are many cases that the system is constructed so that a plurality of the FPDs can be operated by one console. However, in such a case, the FPDs and the console are sometimes placed apart from each other. As a result, in terms of work efficiency, a disadvantage that a radiation engineer who has performed the radiographing cannot confirm the radiographic image immediately after the radiographing, is caused.

Accordingly, it is necessary to place the console near the FPDs, and for example, it is preferable to place the console for each radiographing room. However, the console has a variety of functions, and therefore, the price of one console is high. Accordingly, it has been difficult to increase the number of consoles with respect to the number of FPDs in a conventional technique.

Here, the inventor of the present invention has considered that the functions of each console are limited and the cost thereof is reduced to reduce the price of one console. Then, considering that the radiographic image data detected by each FPD is finally stored in an image storage device of a server (also referred to as a host) in the radiographic imaging system, the inventor has found out that it is not always necessary to transmit an original image of the radiographic image data from the FPD to the console once; generate the confirmation radiographic image data by the console based on the original image and display the confirmation radiographic image data on the display unit; and transmit the original image of the radiographic image data from the console to the image storage device like a conventional system.

Therefore, an object of the present invention is to provide a radiographic image detecting apparatus and a radiographic imaging system which can limit the functions of each console to reduce the cost thereof, reduce the price of one console, increase the number of consoles with respect to the FPDs (the radiographic image detecting apparatuses), and enhance the work efficiency of the radiographing.

Means for Solving the Problem

In order to achieve the above object, in accordance with a first aspect of the present invention, a radiographic image detecting apparatus of the present invention comprises:

a radiation detection unit to detect irradiated radiation;

a storage unit to store radiographic image data based on the radiation detected by the radiation detection unit;

a confirmation radiographic image data generation unit to generate confirmation radiographic image data based on the radiographic image data stored by the storage unit; and a communication unit to transmit the radiographic image data and the confirmation radiographic image data to external instruments which are different from each other, respectively.

Moreover, in the radiographic image detecting apparatus of the present invention, preferably, the confirmation radiographic image data has a smaller amount of data than the radiographic image data.

Moreover, in the radiographic image detecting apparatus of the present invention, preferably, the communication unit transmits the radiographic image data to an image storage device, and transmits the confirmation radiographic image data to a console.

Moreover, in the radiographic image detecting apparatus of the present invention, preferably, the communication unit simultaneously transmits the radiographic image data and the confirmation radiographic image data to the external instruments which are different from each other, respectively.

Moreover, in the radiographic image detecting apparatus of the present invention, preferably, the communication unit transmits the radiographic image data to the image storage device after transmitting the confirmation radiographic image data to the console.

Furthermore, in accordance with a second aspect of the present invention, a radiographic imaging system comprises:

a radiographic image detecting apparatus to detect irradiated radiation and obtain radiographic image data;

a console to operate the radiographic image detecting apparatus, the console comprising a display unit for displaying the obtained radiographic image data; and an image storage device which is communicable with the radiographic image detecting apparatus and the console through a network, wherein the radiographic image detecting apparatus transmits the obtained radiographic image data to the image storage device, and generates confirmation radiographic image data which has a smaller amount of data than the radiographic image data based on the radiographic image data and transmits the confirmation radiographic image data to the console, the image storage device stores the radiographic image data transmitted from the radiographic image detecting apparatus, and the console displays the confirmation radiographic image data transmitted from the radiographic image detecting apparatus on the display unit.

EFFECT OF THE INVENTION

According to the present invention, the radiographic image detecting apparatus comprises the confirmation radiographic image data generation unit to generate the confirmation radiographic image data based on the stored radiographic image data and the communication unit to transmit the radiographic image data and the confirmation radiographic image data to the external instruments which are different from each other, respectively. Therefore, it becomes unnecessary to generate the confirmation radiographic image data from the radiographic image data in the console like a conventional apparatus, and the functions of the console can be reduced. In such a way, the price of one console can be reduced.

As a result, a radiographic image detecting apparatus and a radiographic imaging system which can increase the number of consoles with respect to the radiographic image detecting apparatuses, and enhance the work efficiency of the radiographing, can be provided.

Moreover, according to the present invention, the confirmation radiographic image data has a smaller amount of data than the radiographic image data. Therefore, it becomes unnecessary to store the entire data of the obtained radiographic image data in the console like a conventional apparatus, and the functions of the console can be reduced. In such a way, the price of one console can be reduced.

Moreover, according to the present invention, the communication unit transmits the radiographic image data to the image storage device, and transmits the confirmation radiographic image data to the console. Therefore, it becomes unnecessary to generate the confirmation radiographic image data from the radiographic image data in the console, and a specific configuration in which the functions of the console can be reduced can be achieved.

Moreover, according to the present invention, the communication unit simultaneously transmits the radiographic image data and the confirmation radiographic image data to the external instruments which are different from each other, respectively. Therefore, transmission work of the image data can be performed in a short time.

Moreover, according to the present invention, the communication unit transmits the radiographic image data to the image storage device after transmitting the confirmation radiographic image data to the console. Therefore, the radiographic image data can be transmitted to the image storage device after the radiographing state of the radiographic image data is determined by the confirmation radiographic image data in the console, and useless communication work does not have to be performed.

Furthermore, according to the present invention, the radiographic image detecting apparatus transmits the obtained radiographic image data to the image storage device, generates the confirmation radiographic image data which has a smaller amount of data than the radiographic image data based on the radiographic image data, and transmits the confirmation radiographic image data to the console. The image storage device stores the radiographic image data transmitted from the radiographic image detecting apparatus, and the console displays the confirmation radiographic image data transmitted from the radiographic image detecting apparatus on the display unit. Therefore, it becomes unnecessary to generate the confirmation radiographic image data from the radiographic image data in the console like a conventional system. Further, it also becomes unnecessary to store the entire data of the obtained radiographic image data in the console, and the functions of the console can be reduced. In such a way, the price of one console can be reduced.

BEST MODE FOR CARRYING OUT THE INVENTION

The embodiment of a radiographic image detecting apparatus and a radiographic imaging system according to the present invention will be explained in detail with reference to the drawings. However, the present invention is not limited to the illustrated examples.

First, a configuration of the radiographic imaging system of this embodiment will be explained.

Figure 1:
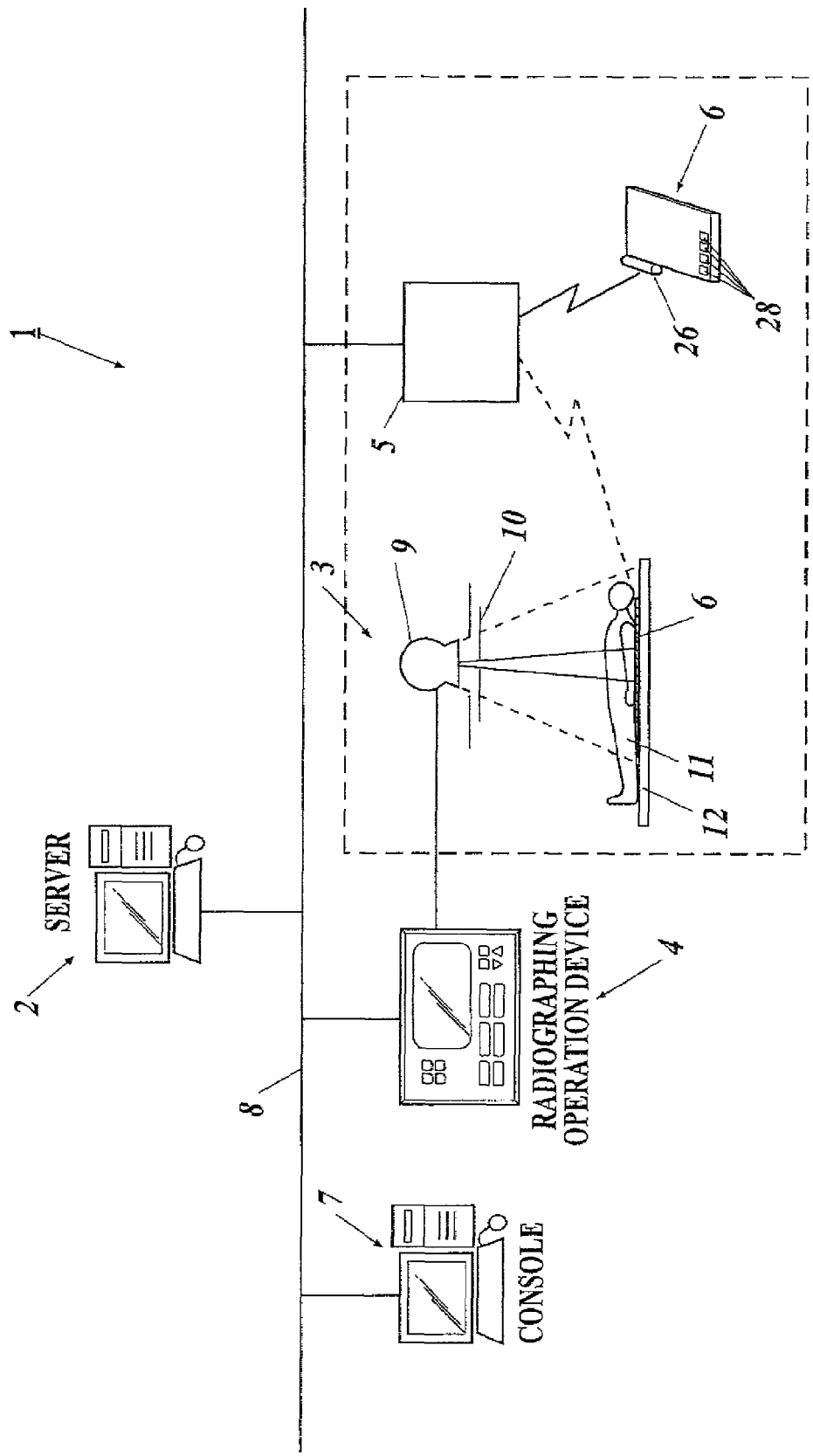
FIG. 1 This is a view showing a schematic configuration of a radiographic imaging system illustrated as an embodiment to which the present invention is applied.

FIG. 1 is a view showing a schematic configuration of an embodiment of the radiographic imaging system to which the present invention is applied.

In the radiographic imaging system 1 according to this embodiment, as shown in FIG. 1, a server 2 that manages information regarding radiographic imaging, a radiographing operation device 4 that performs operations regarding the radiographic imaging, a base station 5 for performing a communication according to a wireless communication mode, for example, such as a wireless LAN (Local Area Network), and a console 7 that operates a radiographic image detecting apparatus 6, are connected to each other through a network 8. A radiographic imaging device 3 that radiographs a radiographic image by irradiating a subject with a radiation is connected to the radiographing operation device 4 through a cable. Here, the network 8 may be a communication line dedicated to the system; however, more preferably, is an existing line, such as Ethernet (registered trademark) or the like, since a degree of freedom in the system configuration is lowered by using the dedicated communication line.

The server 2 is composed of a computer. In the server 2, a control unit that controls the each unit composing the server 2, an input operation unit that receives a variety of information and an instruction of an operator, an external storage device that stores the variety of information, and the like (any of which is not shown), are provided. Moreover, the server 2 of this embodiment functions as an image storage device that finally stores image data obtained by the radiographic image detecting apparatus 6.

The control unit allows the external storage device to store patient information, radiographing information, and the like, which are inputted from the input operation unit, so as to correspond to each other. The patient information is information regarding a patient 11, such as a name, age, gender, and birthday of the patient 11, and a patient ID number for identifying the patient 11, and the like. Moreover, the radiographing information is information necessary to perform the radiographing, such as a radiographed region (a radiographed portion on a body of the radiographed person), radiographing direction and method, and the like.

Moreover, as the image storage device, the control unit of this embodiment temporarily stores the radiographic image data so as to correspond the patient information and the radiographing information when the radiographic image data detected by the radiographic image detecting apparatus 6 is transmitted from the radiographic image detecting apparatus 6.

Furthermore, as described later, as the image storage device, the control unit of this embodiment finally stores the radiographic image data after the radiation engineer confirms that the radiographic image data is in a normal state based on the confirmation radiographic image data displayed on the console 7.

Note that, in place of the server 2, an information reading device such as a card reader that reads the patient information and the radiographing information which are written in an ID card in advance, may be provided.

The radiographic imaging device 3 comprises a radiation source 9, and generates the radiation in such a manner that a tube voltage is applied to the radiation source 9. An aperture stop device 10 that adjusts a radiation irradiation field is provided so as to be freely openable and closable on a radiation irradiation port of the radiation source 9. A bed 12 on which the patient 11 is laid is provided below the radiation source 9 and within a radiation irradiation area.

The radiographing operation device 4 is composed of a computer comprising a display unit that displays the information, and an input operation unit that receives the instruction from the radiation engineer as the operator (any of which is not shown) and the like, and controls the radiation source 9 and the like of the radiographic imaging device 3 so that the radiographing can be performed by a tube voltage value and a dose of the radiation, which correspond to radiographing conditions.

Figure 2:
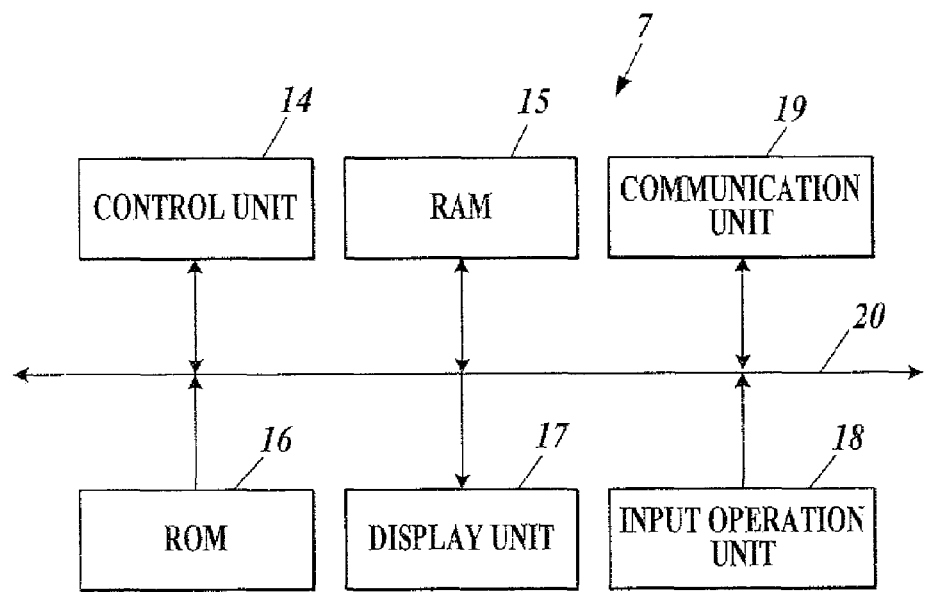
FIG. 2 This is a block diagram showing a main portion configuration of a console composing the radiographic imaging system of FIG. 1.

As shown in FIG. 2, the console 7 comprises a control unit 14, a RAM 15, a ROM 16, a display unit 17, an input operation unit 18, a communication unit 19, and the like. Each unit is connected by a bus 20.

For example, the display unit 17 comprises a CRT (Cathode Ray Tube), an LCD (Liquid Crystal Display), or the like, and displays a variety of screens in accordance with instructions of display signals outputted from the control unit 14 and inputted to the display unit 17. For example, when the radiation engineer performs the radiographing, the confirmation radiographic image data generated in the radiographic image detecting apparatus 6 automatically or according to the instruction from the control unit 14 based on the radiographic image data is transmitted to the console 7, and the confirmation radiographic image data is displayed on the display unit as information for confirming the radiographic image data.

For example, the input operation unit 18 comprises a keyboard, a mouse, and the like, and outputs a depression signal of a key depressed on the keyboard and an operation signal by the mouse as input signals to the control unit 14.

Moreover, in the radiographic imaging system 1 according to this embodiment, a signal related to an instruction for transferring image data of the radiographic image detected by the radiographic image detecting apparatus 6 may be outputted to the control unit 14 based on a predetermined operation of the input operation unit 18. Specifically, in the system, it can be selectable by the radiation engineer whether the image data is to be transferred every time when the radiographing of each radiographic image is ended, or the image data of the patient 11 is transferred in a lump every time when the radiographing of the radiographic images for the one patient 11 is ended, or all of the image data are transferred in a lump after the radiographing of all of radiographic images, which is scheduled in the radiographic imaging device 3, is ended.

Furthermore, based on a predetermined operation of the input operation unit 18, a signal related to an instruction for deleting the image data of the radiographic image stored in the radiographic image detecting apparatus 6 is outputted to the control unit 14.

The communication unit 19 communicates a variety of information between the radiographic image detecting apparatus 6 and the server 2 through the base station 5 according to the wireless communication mode such as the wireless LAN.

For example, the control unit 14 comprises a CPU and the like, reads out predetermined programs stored in the ROM 16 and expands the programs to a work area of the RAM 15, and executes variety of processing in accordance with the programs.

In particular, the control unit 14 receives the information of the patients scheduled to be radiographed by using the radiographic image detecting apparatus as an operation target and the radiographing information from the server 2 through the network 8, generates a list in which a plurality of pieces of received information are arrayed in a radiographing order, and stores the list in a memory (not shown). With regard to the patient information and the radiographing information, the control unit 14 may receive the information inputted from a terminal such as another computer placed in a consulting room or the like and connected to the network 8. Moreover, the patient information and the radiographing information, which are written in an ID card in advance and read out by an information reading device such as a card reader connected to the console 7 by a cable or the like, may be inputted.

Moreover, the control unit 14 may wirelessly transmit information regarding the radiographed region among the received radiographing information to the radiographic image detecting apparatus 6 through the base station 5.

Moreover, when an instruction for indicating that the re-radiographing is not performed again is inputted from the input operation unit 18, the control unit 14 may allow the display unit 17 to display a message for prompting of the selection of the timing to transfer the image data of the radiographic image from the radiographic image detecting apparatus 6, by the input operation unit 18.

Then, for example, when the transfer timing of the image data is selected by a predetermined operation of the input operation unit 18, the control unit 14 allows the display unit 17 to display the patient information and the radiographing information, which are related to the radiographing performed next, based on the list.

The transfer timing of the image data may be selected and set by the input operation unit 18 in advance. In this case, when the instruction for indicating that the re-radiographing is not performed again is inputted from the input operation unit 18, the patient information and the radiographing information, which are related to the radiographing performed next, may be displayed on the display unit 17.

Moreover, based on an instruction inputted from the input operation unit 18, the control unit 14 may allow the radiographic image detecting apparatus 6 to transfer the image data.

Furthermore, based on an instruction inputted from the input operation unit 18, the control unit 14 allows the radiographic image detecting apparatus 6 to delete the image data stored therein.

Still further, as described above, the patient information and the radiographing information may be inputted from the other device (for example, the computer in the consulting room, a computer in a reception, and the like) such as the server 2, or may be inputted from the console 7.

Figure 3:
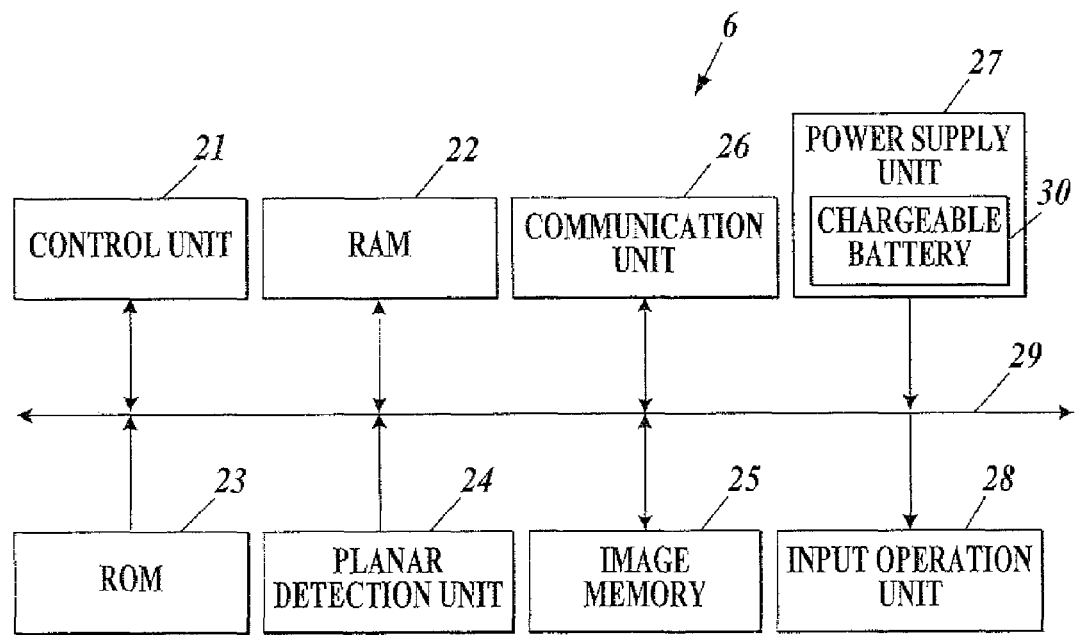
FIG. 3 This is a block diagram showing a main portion configuration of a radiographic image detecting apparatus composing the radiographic imaging system of FIG. 1.

For example, the radiographic image detecting apparatus 6 is a cassette-shaped FPD. As shown in FIG. 3, the radiographic image detecting apparatus 6 comprises a control unit 21 that also serves as a confirmation radiographic image data generation unit, a RAM 22, a ROM 23, a planar detection unit 24 as a radiation detection unit, an image memory 25 as a storage unit, a communication unit 26, a power supply unit 27, an input operation unit 28, and the like. Each unit is connected through a bus 29.

For example, the planar detection unit 24 comprises a glass substrate and the like. On a predetermined position of the substrate, a plurality of pixels which detect the radiation irradiated from the radiation source 9 and at least transmitted through the subject in response to intensity thereof, and convert the detected radiation into electrical signals and store the electrical signals, are arrayed in a matrix.

Here, for example, as the planar detection unit 24, an indirect type of one which comprises a radiation-light conversion layer that converts the radiation into fluorescence (light), and a photoelectric conversion layer that detects the fluorescence converted by the radiation-light conversion layer and coverts the fluorescence into the electrical signals; a direct type of one which comprises a radiation-electrical signal conversion layer having a radiation receiving portion that directly converts the radiation into electric charges in place of the radiation-light conversion layer and the photoelectric conversion layer; and the like, are exemplified but not shown in the drawings.

For example, the image memory 25 comprises a nonvolatile memory such as a flash memory, and stores the image data of the radiographic image, which is obtained by reading the electrical signals accumulated in the planar detection unit 24.

The communication unit 26 communicates a variety of information between the console 7 and the server 2 through the base station 5 according to the wireless communication mode such as the wireless LAN.

The power supply unit 27 comprises a chargeable battery 30 that supplies a power supply to each unit composing the radiographic image detecting apparatus 6, and is composed so as to be chargeable through charging terminals (not shown) provided on predetermined positions of the radiographic image detecting apparatus 6.

On one surface of a casing of the radiographic image detecting apparatus 6, the input operation unit 28 that receives the instruction from the radiation engineer may be provided.

For example, the control unit 21 comprises a CPU (Central Processing Unit) and the like, reads out predetermined programs stored in the ROM 23 and expands the programs to a work area of the RAM 22, and executes variety of processings in accordance with the programs.

Specifically, for example, the control unit 21 controls switching units of TFTs (Thin Film Transistors) or the like composing each pixel of the planar detection unit 24, switches the reading of the electrical signals stored in each pixel, and reads the electrical signals stored in the planar detection unit 24. As a result, the image data of the radiographic image is obtained from the planar detection unit 24.

Moreover, as the confirmation radiographic image data generation unit, the control unit 21 generates the confirmation radiographic image data (image data of a reduced image such as a so-called thumbnail image) having a smaller amount of data than the radiographic image data based on the obtained radiographic image data. The generated confirmation radiographic image data is transmitted to the console 7, and the radiation engineer as the operator confirms the radiographing on the display unit of the console.

As the confirmation radiographic image data, an original image of the radiographic image data (radiographic image data which is in a state of remaining to be detected by the radiographic image detecting apparatus 6 or in a state close to the above state) may be used for the confirmation. However, preferably, the confirmation radiographic image data is the one having a smaller amount of data than the original image of the radiographic image data because the functions of the console can be reduced in that it becomes unnecessary to store and process the entire data of the radiographic image data in the console 7.

Figure 4:
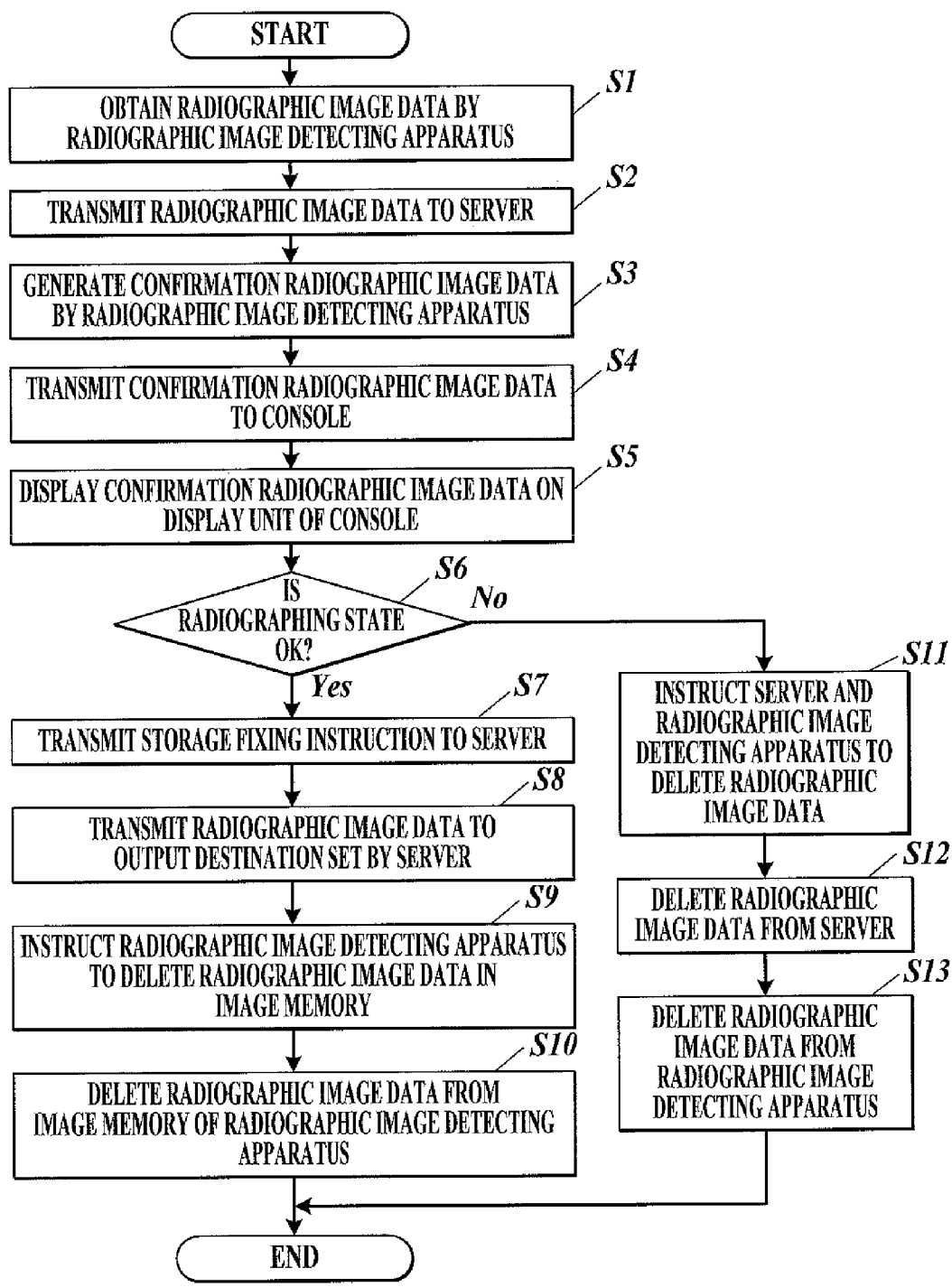
FIG. 4 This is a flowchart showing a flow of processing in the radiographic imaging system of this embodiment.

Next, functions of the radiographic imaging system 1 will be explained by using a flowchart of FIG. 4.

When the radiographing of the radiographic image is performed, first, a doctor reserves the radiographing by the computer in the consulting room. Then, the reservation is transmitted through the server 2 to the console 7 provided in front of a radiographing room. Specifically, the patient information and the radiographing information are transmitted from the server 2 to the radiographing operation device 4. The radiographing operation device 4 appropriately displays the received information on the display unit. The radiation engineer radiographs the radiographic image while confirming the information. The patient information and the radiographing information may be transmitted also to the radiographic image detecting apparatus 6 to be used.

Based on the tube voltage value and the dose of the radiation which are included in the received radiographing information, the radiographing operation device 4 controls the radiation source 9 and the like of the radiographic imaging device 3. The radiographic imaging device 3 irradiates the patient 11 with the radiation under these conditions.

At this time, the radiographic image detecting apparatus 6 is inserted on the bed 12 and under the patient 11, the dose of the radiation transmitted through the patient 11 is detected by the planar detection unit 24, the detected radiation is converted into the electrical signals, and the radiographic image data is obtained (Step S1). Then, the obtained radiographic image data is stored in the image memory 25 so as to correspond to the patient information, the radiographing information, and the like, and is transmitted from the communication unit 26 to the image storage device (the server 2 in this embodiment). The server 2 stores the radiographic image data (Step S2). At this time, a variety of image correction processing may be performed. As the processing, for example, offset correction, gain correction, noise removal correction, image defect correction, gradation processing, frequency processing, and the like, are exemplified. Moreover, the radiographic image data for which the correction processing has been carried out may be transmitted to the server 2, and the confirmation radiographic image data to be described later may be generated based on the radiographic image data for which the correction processing has been carried out.

The control unit 21 of the radiographic image detecting apparatus 6 is the confirmation radiographic image data generation unit, and generates the confirmation radiographic image data (the thumbnail image) having smaller amount of data than the radiographic image data based on the obtained radiographic image data (Step S3). Specifically, the confirmation radiographic image data is the one in which the amount of data is generally reduced to approximately $1/100$ to $1/10000$ of the original image. Then, the communication unit 26 transmits the confirmation radiographic image data to the corresponding console 7 (Step S4).

The communication unit 26 transmits the radiographic image data and the confirmation radiographic image data to external instruments which are different from each other, respectively. In this embodiment, as described above, the communication unit 26 transmits the radiographic image data to the image storage device (the server 2), and transmits the generated confirmation radiographic image data to the console 7. Moreover, the processing in Steps S2 to S4 is performed at substantially the same time. Exactly, in some cases, a processing order of Steps S2 and S3 is reversed, the processing is performed in an order of Steps S3, S4 and S2, and Steps S2 and S4 are performed simultaneously after the processing of Step S3 is performed.

When the console 7 receives the confirmation radiographic image data, the control unit 14 allows the display unit 17 to display the confirmation radiographic image data (Step S5). Here, the radiation engineer confirms a radiographing state (for example, confirms whether or not a position of the subject is shifted (a region of interest is lost) and whether or not the image is blurred) (Step S6). When it is determined that the radiographing state is normal, a signal for indicating the above state (a storage fixing instruction) is transmitted from the console 7 to the server 2 by a predetermined operation of the engineer (Step S7). The server 2 fixes the final storage of the radiographic image data corresponding to the confirmation radiographic image data, and transmits the radiographic image data to a set output destination (for example, a monitor, printer, and the like of the consulting room) (Step S8). At this time, it is preferable that the image processing corresponding to output characteristics of each set output destination is added in the server 2 and the radiographic image data is transmitted to each output destination from a viewpoint of equalizing (matching) the appearance of the radiographed image over the output destinations. Moreover, a signal for instructing the deletion of the radiographic image data in the image memory 25 is transmitted from the console 7 to the radiographic image detecting apparatus 6 by a predetermined operation of the engineer (Step S9). Then, the control unit 21 of the radiographic image detecting apparatus 6 deletes the radiographic image data and the confirmation radiographic image data in the image memory 25 (Step S10). With regard to the performing order of Steps S7 and S9, it is preferable that Step S7 is performed first and Step S9 be performed later in consideration for the accident where the radiographic image data in the server 2 is deleted owing to an unforeseen circumstances.

On the other hand, when the radiographing state is confirmed by the radiologist and it is determined that the radiographing state is not normal, a signal for indicating the above state (an instruction for deleting the radiographic image data) is transmitted to the server 2 and the radiographic image detecting apparatus 6 by a predetermined operation of the engineer (Step S11). Then, the server 2 deletes the radiographic image data corresponding to the confirmation radiographic image data (Step S12). Moreover, the radiographic image detecting apparatus 6 deletes the radiographic image data and the confirmation radiographic image data in the image memory 25 (Step S13), and performs the radiographing one more time.

The radiographic image data stored in the image memory 25 of the radiographic image detecting apparatus 6 may be deleted based on an obtaining completion signal from the server 2 when the radiographic image data detected first is transmitted to the server 2.

Moreover, the confirmation radiographic image data stored in the image memory 25 of the radiographic image detecting apparatus 6 may be deleted based on an obtaining completion signal from the console 7 when the confirmation radiographic image data is transmitted to the console 7 in Step s4.

Moreover, in this embodiment, the communication unit 26 simultaneously transmits the radiographic image data and the confirmation radiographic image data; however, the present invention is not limited to this. For example, the confirmation radiographic image data is displayed on the console 7 after the communication unit 26 transmits the confirmation radiographic image data to the console 7. When the result of the confirmation is OK, the console 7 may transmit an OK signal to the radiographic image detecting apparatus 6, and the radiographic image detecting apparatus 6 may transmit the radiographic image data to the image storage device (the server 2) based on the reception of the OK signal.

Figure 5:
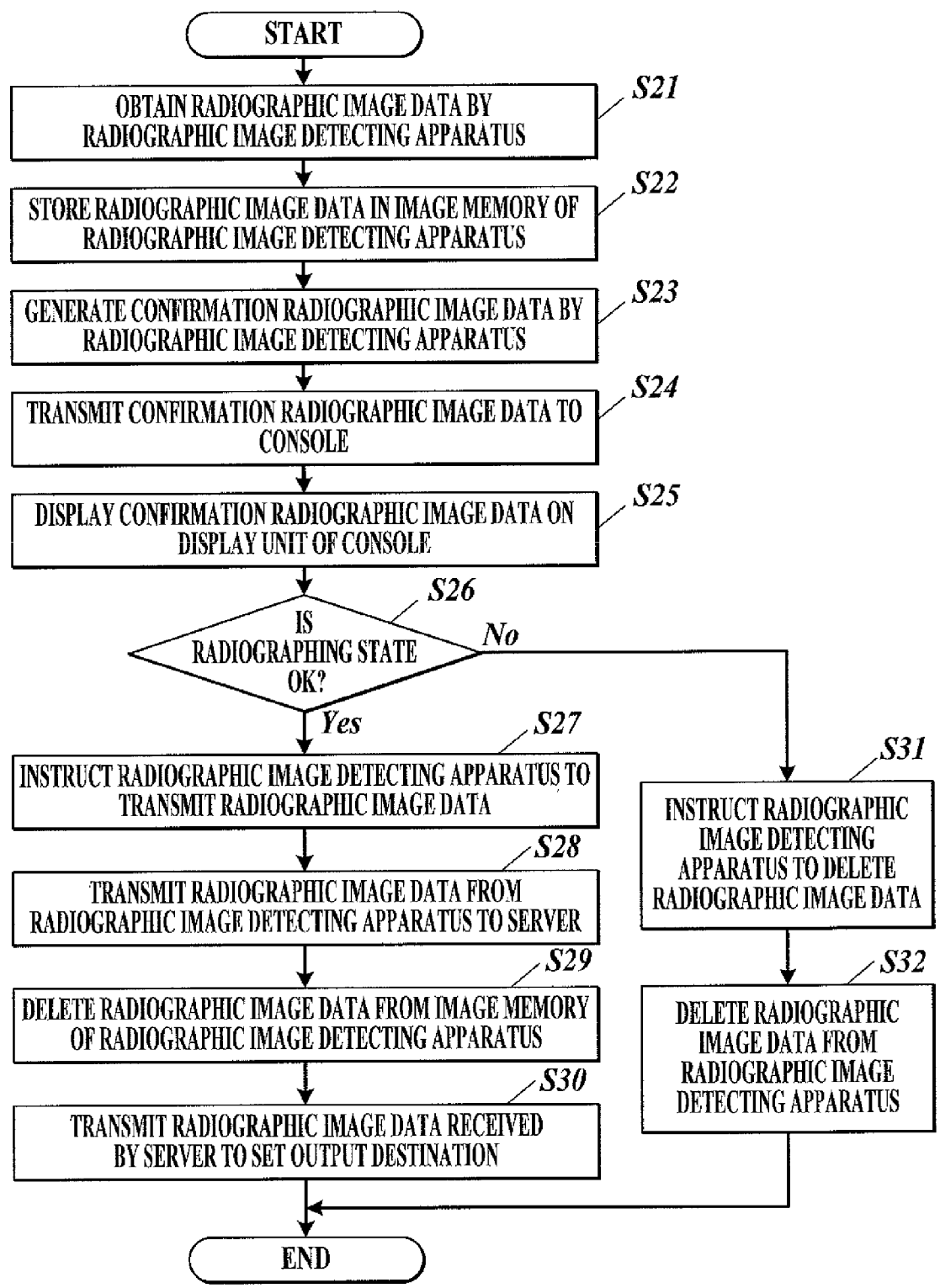
FIG. 5 This is a flowchart showing another example of a flow of processing in the radiographic imaging system of this embodiment.

Hereinafter, another example will be explained in detail by using a flowchart of FIG. 5.

When the radiographing of the radiographic image is performed, first, the doctor reserves the radiographing by the computer in the consulting room. Then, the reservation is transmitted through the server 2 to the console 7 provided in front of the radiographing room. Specifically, the patient information and the radiographing information are transmitted from the server 2 to the radiographing operation device 4. The radiographing operation device 4 appropriately displays the received information on the display unit. The radiation engineer radiographs the radiographic image while confirming the information. The patient information and the radiographing information may be transmitted also to the radiographic image detecting apparatus 6 to be used.

Based on the tube voltage value and the dose of the radiation which are included in the received radiographing information, the radiographing operation device 4 controls the radiation source 9 and the like of the radiographic imaging device 3. The radiographic imaging device 3 irradiates the patient 11 with the radiation under these conditions.

At this time, the radiographic image detecting apparatus 6 is inserted on the bed 12 and under the patient 11, the dose of the radiation transmitted through the patient 11 is detected by the planar detection unit 24, the detected radiation is converted into the electrical signals, and the radiographic image data is obtained (Step S21). Then, the obtained radiographic image data is stored in the image memory 25 so as to correspond to the patient information, the radiographing information, and the like (Step S22). At this time, the variety of image correction processing may be performed. As the processing, for example, offset correction, gain correction, noise removal correction, image defect correction, gradation processing, frequency processing, and the like, are exemplified. Moreover, the confirmation radiographic image data may be generated after the correction processing.

The control unit 21 of the radiographic image detecting apparatus 6 is the confirmation radiographic image data generation unit, and generates the confirmation radiographic image data (the thumbnail image) having a smaller amount of data than the radiographic image data based on the obtained radiographic image data (Step S23). Specifically, the confirmation radiographic image data is the one in which the amount of data is generally reduced to approximately 1/100 to 1/10000 of the original image. Then, the communication unit 26 transmits the confirmation radiographic image data to the corresponding console 7 (Step S24). After the confirmation radiographic image data (the thumbnail image) is generated, the above-described image correction processing may be carried out for the image data, and the thumbnail image for which the correction processing is carried out may be transmitted to the console 7. In such way, in comparison with the case of performing the correction processing for the radiographic image data, a processing time can be shortened.

The communication unit 26 transmits the radiographic image data and the confirmation radiographic image data to the external instruments which are different from each other, respectively. In this example, the communication unit 26 transmits the generated confirmation radiographic image data to the console 7 as described above, and transmits the radiographic image data to the image storage device (the server 2) as described later. Moreover, the processing in Steps S22 to S24 is performed at substantially the same time. Exactly, in some cases, a processing order of Steps S22 and S23 is reversed, the processing is performed in an order of Steps S23, S24 and S22, and Steps S22 and S24 are performed simultaneously after the processing of Step S23 is performed.

When the console 7 receives the confirmation radiographic image data, the control unit 14 allows the display unit 17 to display the confirmation radiographic image data (Step S25). Here, the radiation engineer confirms the radiographing state (for example, confirms whether or not a position of the subject is shifted (a region of interest is lost) and whether or not the image is blurred) (Step S26). When it is determined that the radiographing state is normal, a signal (an OK signal) for instructing that the radiographic image data in the image memory 25 is transmitted to the server 2, is transmitted from the console 7 to the radiographic image detecting apparatus 6 by a predetermined operation of the engineer (Step S27). Then, the control unit 21 of the radiographic image detecting apparatus 6 transmits the radiographic image data corresponding to the confirmation radiographic image data or the radiographic image data for which the above-described image correction processing is carried out from the communication unit 26 to the server 2 (Step S28). Moreover, after the radiographic image data or the radiographic image data for which the above-described image correction processing is carried out is transmitted to the server 2, the control unit 21 of the radiographic image detecting apparatus 6 deletes the radiographic image data and the confirmation radiographic image data in the image memory 25 (Step S29). Then, the server 2 stores the received radiographic image data, and transmits the radiographic image data to a set output destination (for example, the monitor, printer, and the like of the consulting room) (Step S30).

When the server 2 obtains the radiographic image data for which the image correction processing is carried out by the radiographic image detecting apparatus 6, it is preferable that the image processing corresponding to the output characteristics of each set output destination is added in the server 2 and the radiographic image data is transmitted to each output destination from a viewpoint of equalizing (matching) the appearance of the radiographed image over the output destinations.

Meanwhile, when the server 2 obtains the radiographic image data (the radiographic image data for which the image correction processing is not carried out by the radiographic image detecting apparatus 6), it is preferable that the variety of correction processing is carried out, the image processing corresponding to the output characteristics of each set output destination is further added in the server 2, and the radiographic image data is transmitted to each output destination, from a viewpoint of equalizing (matching) the appearance of the radiographed image over the output destinations.

On the other hand, when the radiographing state is confirmed by the radiation engineer and it is determined that the radiographing state is not normal, a signal for indicating the above state (an instruction for deleting the radiographic image data) is transmitted to the radiographic image detecting apparatus 6 by a predetermined operation of the engineer (Step S31). Then, the radiographic image detecting apparatus 6 deletes the radiographic image data and the confirmation radiographic image data in the image memory 25 (Step S32), and performs the radiographing one more time.

The confirmation radiographic image data stored in the image memory 25 of the radiographic image detecting apparatus 6 may be deleted based on an obtaining completion signal from the console 7 when the confirmation radiographic image data is transmitted to the console 7 in Step S24.

As described above, the radiographic image detecting apparatus of this embodiment comprises: the confirmation radiographic image data generation unit to generate the confirmation radiographic image data based on the stored radiographic image data; and the communication unit to transmit the radiographic image data and the confirmation radiographic image data to the external instruments which are different from each other, respectively. Therefore, it becomes unnecessary to generate the confirmation radiographic image data from the radiographic image data in the console like a conventional apparatus, and the functions of the console can be reduced. In such a way, the price of one console can be reduced.

Moreover, in this embodiment, the confirmation radiographic image data has a smaller amount of data than the radiographic image data. Therefore, it becomes unnecessary to store the entire data of the obtained radiographic image data in the console like a conventional apparatus, and the functions of the console can be reduced. In such a way, the price of one console can be reduced.

Furthermore, in this embodiment, the communication unit transmits the radiographic image data to the image storage device, and transmits the confirmation radiographic image data to the console. Therefore, it becomes unnecessary to generate the confirmation radiographic image data from the radiographic image data in the console, and a specific configuration in which the functions of the console can be reduced can be achieved.

Still further, in this embodiment, the communication unit simultaneously transmits the radiographic image data and the confirmation radiographic image data to the external instruments which are different from each other, respectively. Therefore, transmission work of the image data can be performed in a short time.

Moreover, in another example described above, the communication unit transmits the radiographic image data to the image storage device after transmitting the confirmation radiographic image data to the console. Therefore, the radiographic image data can be transmitted to the image storage device after the radiographing state of the radiographic image data is determined by the confirmation radiographic image data in the console, and useless communication work does not have to be performed.

Moreover, in accordance with the radiographic imaging system of this embodiment, the radiographic image detecting apparatus transmits the obtained radiographic image data to the image storage device, generates the confirmation radiographic image data which has a smaller amount of data than the radiographic image data based on the radiographic image data, and transmits the confirmation radiographic image data to the console. The image storage device stores the radiographic image data transmitted from the radiographic image detecting apparatus, and the console displays the confirmation radiographic image data transmitted from the radiographic image detecting apparatus on the display unit. Therefore, it becomes unnecessary to generate the confirmation radiographic image data from the radiographic image data in the console like a conventional system. Further, it also becomes unnecessary to store the entire data of the obtained radiographic image data in the console, and the functions of the console can be reduced. In such a way, the price of one console can be reduced.

As a result, a radiographic imaging system which can increase the number of consoles with respect to the radiographic image detecting apparatuses, and enhance the work efficiency of the radiographing, can be provided.

Moreover, when the number of parts composing the console can be reduced by reducing the functions, the console can be downsized.

Furthermore, when the variety of image correction processing and the correction inherent to the radiographic image detecting apparatus are performed in the console, each console must always hold and manage the latest information. However, when the variety of image correction processing and the correction processing inherent to the radiographic image detecting apparatus are performed in the server, the server manages the system in a lump. As a result, the system management is facilitated.

The above description in this embodiment merely illustrates one example of the preferred radiographic image detecting apparatus and radiographic imaging system according to the present invention and the present invention is not limited to the description in this embodiment.

For example, a variety of correction processing may be performed for the radiographic image data detected by the radiographic image detecting apparatus. Here, the correction processing may be performed in the server (the image storage device) in which correction data are provided. Moreover, the correction processing may be performed in the radiographic image detecting apparatus in which the correction data are provided. Furthermore, when a plurality of the correction processings are performed, the server and the radiographic image detecting apparatus may perform the correction processings in a dividing manner by dividing and managing the correction data in both of the server and the radiographic image detecting apparatus.

Moreover, in this embodiment, the variety of information including the radiographic image data, which is obtained by the radiographic image detecting apparatus, is transmitted and received by the communication means according to the wireless communication mode. However, the present invention is not limited to this. The variety of information may be transmitted and received by communication means according to a wired communication mode through a cable.

Furthermore, in this embodiment, the server is composed so as to also function as the image storage device; however, the present invention is not limited to this.

For example, in the system, an image storage device which only has a function to store information such as the radiographic image data may be provided separately from the server which performs the information management and the like.

Besides the above, it is possible to appropriately modify detailed configurations and detailed operations of each element of the radiographic imaging system in this embodiment without departing from the gist of the present invention.

INDUSTRIAL APPLICABILITY

As described above, the radiographic image detecting apparatus and the radiographic imaging system according to the present invention can be applied to the system that transmits the obtained radiographic image data from the radiographic image detecting apparatus to the different external instruments. In particular, the system can be suitably applied to a system that can transmit the obtained radiographic image data from the radiographic image detecting apparatus to the image storage device, and generate the confirmation radiographic image data which has a small amount of data based on the information and transmit the generated confirmation radiographic image data to the console.

The invention claimed is:

1. A radiographic image detecting apparatus, comprising:
   a radiation detection unit to detect irradiated radiation;
   a storage unit to store radiographic image data based on the radiation detected by the radiation detection unit;
   a confirmation radiographic image data generation unit to generate confirmation radiographic image data having a smaller amount of data than the radiographic image data based on the radiographic image data stored by the storage unit; and
   a communication unit transmitting the radiographic image data to an image storage device and transmitting the confirmation radiographic image data to a console, the image storage device and the console are different from each other, respectively.

2. The radiographic image detecting apparatus of claim 1, wherein the communication unit simultaneously transmits the radiographic image data and the confirmation radiographic image data.

3. The radiographic image detecting apparatus of claim 1, wherein the communication unit transmits the radiographic image data to the image storage device after transmitting the confirmation radiographic image data to the console.

4. A radiographic imaging system, comprising:
   a radiographic image detecting apparatus to detect irradiated radiation and obtain radiographic image data;
   a console to operate the radiographic image detecting apparatus, the console comprising a display unit for displaying the obtained radiographic image data; and
   an image storage device which is communicable with the radiographic image detecting apparatus and the console through a network,
   wherein the radiographic image detecting apparatus transmits the obtained radiographic image data to the image storage device, and generates confirmation radiographic image data which has a smaller amount of data than the radiographic image data based on the radiographic image data and transmits the confirmation radiographic image data to the console,
   the image storage device stores the radiographic image data transmitted from the radiographic image detecting apparatus, and
   the console displays the confirmation radiographic image data transmitted from the radiographic image detecting apparatus on the display unit.

* * * * *